US009731455B2

(12) United States Patent
Meredith et al.

(10) Patent No.: US 9,731,455 B2
(45) Date of Patent: Aug. 15, 2017

(54) CHOPPED FIBER COMPOSITE SORTING AND MOLDING SYSTEMS AND METHODS

(71) Applicant: The Boeing Company, Huntington Beach, CA (US)

(72) Inventors: Kimberly D. Meredith, Newcastle, WA (US); Morteza Safai, Newcastle, WA (US); Sahrudine Apdalhaliem, Seattle, WA (US); William B. Avery, Enumclaw, WA (US)

(73) Assignee: The Boeing Company, Chicago, IL (US)

( * ) Notice: Subject to any disclaimer, the term of this patent is extended or adjusted under 35 U.S.C. 154(b) by 454 days.

(21) Appl. No.: 14/476,611

(22) Filed: Sep. 3, 2014

(65) Prior Publication Data

US 2016/0059450 A1    Mar. 3, 2016

(51) Int. Cl.
  *B29C 70/58*  (2006.01)
  *B07C 5/36*   (2006.01)
  (Continued)

(52) U.S. Cl.
  CPC ............. *B29C 70/58* (2013.01); *B07C 5/04* (2013.01); *B07C 5/34* (2013.01); *B07C 5/3422* (2013.01); *B07C 5/3425* (2013.01); *B07C 5/368* (2013.01); *B29B 17/02* (2013.01); *B29C 31/045* (2013.01); *B29C 31/085* (2013.01); *B29C 70/12* (2013.01); *B29C 70/14* (2013.01); *B29C 70/62* (2013.01); *B07C 2501/0018* (2013.01);
  (Continued)

(58) Field of Classification Search
  CPC ........................................ B07C 5/366
  See application file for complete search history.

(56) References Cited

U.S. PATENT DOCUMENTS 5,529,169 A *  6/1996  Wilbur .......... B07C 5/366
                                                209/576
6,646,218 B1 * 11/2003 Campbell ........ A24B 1/04
                                                209/577
(Continued)

FOREIGN PATENT DOCUMENTS

EP       1 449 630       8/2004
WO       WO 00/58035    10/2000
(Continued)

OTHER PUBLICATIONS

European Patent Office, Extended European Search Report for related European patent application EP 15183439, Feb. 8, 2016.

*Primary Examiner* — Benjamin Schiffman
(74) *Attorney, Agent, or Firm* — DASCENZO Intellectual Property Law, P.C

(57) ABSTRACT

Chopped fiber composite systems and methods are disclosed. Sorting systems include a conveyor, an imager, a plurality of receptacles, a pneumatic device, and controller. Molding systems include a conveyor, an imager, a mold, a pneumatic device, and a controller. The controller directs the pneumatic device to alter the freefall of chopped fiber composite pieces based on characteristics of the chopped fiber composite pieces as they drop from the conveyor and into a receptacle or a mold. Sorting and molding methods include dropping chopped fiber composite pieces, detecting characteristics of the dropping pieces, and directing the pieces based on the detected characteristics.

20 Claims, 2 Drawing Sheets

(51) Int. Cl.
  *B07C 5/34*    (2006.01)
  *B07C 5/342*   (2006.01)
  *B07C 5/04*    (2006.01)
  *B29C 70/62*   (2006.01)
  *B29C 70/14*   (2006.01)
  *B29C 70/12*   (2006.01)
  *B29C 31/04*   (2006.01)
  *B29C 31/08*   (2006.01)
  *B29B 17/02*   (2006.01)
  *B29L 31/30*   (2006.01)
  *B29K 105/26*  (2006.01)
  *B29K 105/14*  (2006.01)
  *B29K 105/12*  (2006.01)
  *B29K 105/06*  (2006.01)

(52) U.S. Cl.
  CPC ... *B29B 2017/0279* (2013.01); *B29K 2105/06* (2013.01); *B29K 2105/12* (2013.01); *B29K 2105/14* (2013.01); *B29K 2105/26* (2013.01); *B29L 2031/3097* (2013.01); *Y02W 30/622* (2015.05)

(56) References Cited

U.S. PATENT DOCUMENTS 9,028,731 B2* 5/2015 Weyant ............... B29B 17/0042
                                              264/37.1
2004/0222541 A1* 11/2004 Moriwaki ............ B07C 5/3425
                                              264/40.1
2015/0224544 A1* 8/2015 McGloughlin ........ B07C 5/342
                                              209/577

FOREIGN PATENT DOCUMENTS

WO  WO 2011/116030   9/2011
WO  WO 2014/037290   3/2014

* cited by examiner

US 9,731,455 B2

CHOPPED FIBER COMPOSITE SORTING AND MOLDING SYSTEMS AND METHODS

FIELD

The present disclosure relates to chopped fiber composite sorting and molding.

BACKGROUND

Compression molding with chopped fiber composites is used in a variety of industries to produce a variety of parts. For example, the aerospace, land vehicle, and marine vehicle industries are utilizing composite materials more and more, and compression molding is but one available process for manufacturing parts. In the aerospace industry, for example, compression molding may be used for non-critical parts, that is, parts whose failure are not catastrophic to a larger apparatus as a whole. Historically, compression molding with chopped fiber composites has resulted in a lower than desired quality of part due to differences in properties and/or the presence of defects in the chopped fiber composite pieces being utilized. Accordingly, there is a need for improved chopped fiber composite sorting and molding systems and methods, optionally for use to create critical parts, that is, parts whose failure may be significant to the integrity of a larger apparatus as a whole.

SUMMARY

Chopped fiber composite systems and methods are disclosed, including systems and methods for sorting chopped fiber composite pieces and systems and methods for molding fiber-reinforced composite structured from chopped fiber composite pieces.

Systems for sorting chopped fiber composite pieces include a conveyor configured to drop chopped fiber composite pieces, an imager positioned relative to the conveyor and configured to image chopped fiber composite pieces as they drop from the conveyor, a plurality of receptacles positioned relative to the conveyor, a pneumatic device positioned relative to the conveyor and configured to direct pressurized streams of gas at individual chopped fiber composite pieces as they drop from the conveyor, and a controller in communication with the imager and the pneumatic device. The controller is programmed to cause the pneumatic device to direct a specific pressurized stream of gas at a corresponding specific chopped fiber composite piece as it drops from the conveyor based on image data associated with the corresponding specific chopped fiber composite piece and received from the imager. The specific pressurized stream of gas alters the corresponding specific chopped fiber composite piece's freefall path into a predetermined one of the plurality of receptacles based on predetermined criteria determined from the image data associated with the corresponding specific chopped fiber composite piece.

Systems for molding fiber-reinforced composite structures include a conveyor configured to drop chopped fiber composite pieces, an imager positioned relative to the conveyor and configured to image chopped fiber composite pieces as they drop from the conveyor, a mold positioned relative to the conveyor to receive the chopped fiber composite pieces as they drop from the conveyor, a pneumatic device positioned relative to the conveyor and configured to direct pressurized streams of gas at individual chopped fiber composite pieces as they drop from the conveyor, and a controller in communication with the imager and the pneumatic device. The controller is programmed to cause the pneumatic device to direct a specific pressurized stream of gas at a corresponding specific chopped fiber composite piece as it drops from the conveyor based on image data associated with the corresponding specific chopped fiber composite piece and received from the imager. The specific pressurized stream alters the corresponding specific chopped fiber composite piece's freefall path into a predetermined region of the mold and/or alters the orientation of the corresponding specific chopped fiber composite piece based on predetermined criteria determined from the image data associated with the corresponding specific chopped fiber composite piece.

Methods for sorting chopped fiber composite pieces include dropping chopped fiber composite pieces, detecting characteristics of individual chopped fiber composite pieces as they drop, and directing individual ones of the chopped fiber composite pieces into a predetermined receptacle based on one or more detected characteristics of respective individual ones of the chopped fiber composite pieces as they drop.

Methods of molding fiber-reinforced composite structures include dropping chopped fiber composite pieces, detecting characteristics of individual chopped fiber composite pieces as they drop, directing individual ones of the chopped fiber composite pieces into a predetermined region of a mold and/or altering orientations of individual ones of the chopped fiber composite pieces based on one or more detected characteristics of respective individual ones of the chopped fiber composite pieces as they drop, compressing the chopped fiber composite pieces within the mold, and curing the compressed chopped fiber composite pieces to define the fiber-reinforced composite structure.

DESCRIPTION

Chopped fiber composite systems and methods are disclosed herein. Generally, in the figures, elements that are likely to be included in a given example are illustrated in solid lines, while elements that are optional to a given example are illustrated in broken lines. However, elements that are illustrated in solid lines are not essential to all examples of the present disclosure, and an element shown in solid lines may be omitted from a particular example without departing from the scope of the present disclosure.

As used herein, "chopped fiber composite" and "chopped fiber composite pieces" generally refer to a class of composite material used in a compression molding process, in which the composite material is composed of numerous small (e.g., greatest dimension typically in the range of 5-20 mm) pieces, chips, flakes, sheets, and/or other structures having fibers embedded in a polymer. The fibers may be carbon fibers, boron fibers, aramid (e.g., Kevlar®) fibers, glass fibers, and/or other materials, and the polymer may be a thermoset plastic, a thermoplastic, a resin, an epoxy, and/or other materials and may be pre-cured, uncured, or partially cured prior to the compression molding process. A volume of chopped fiber composite pieces are placed in a mold, compressed, and then heated to melt and cure the polymer into the form of the mold, resulting in a fiber-reinforced composite structure, part, or component.

Figure 1:
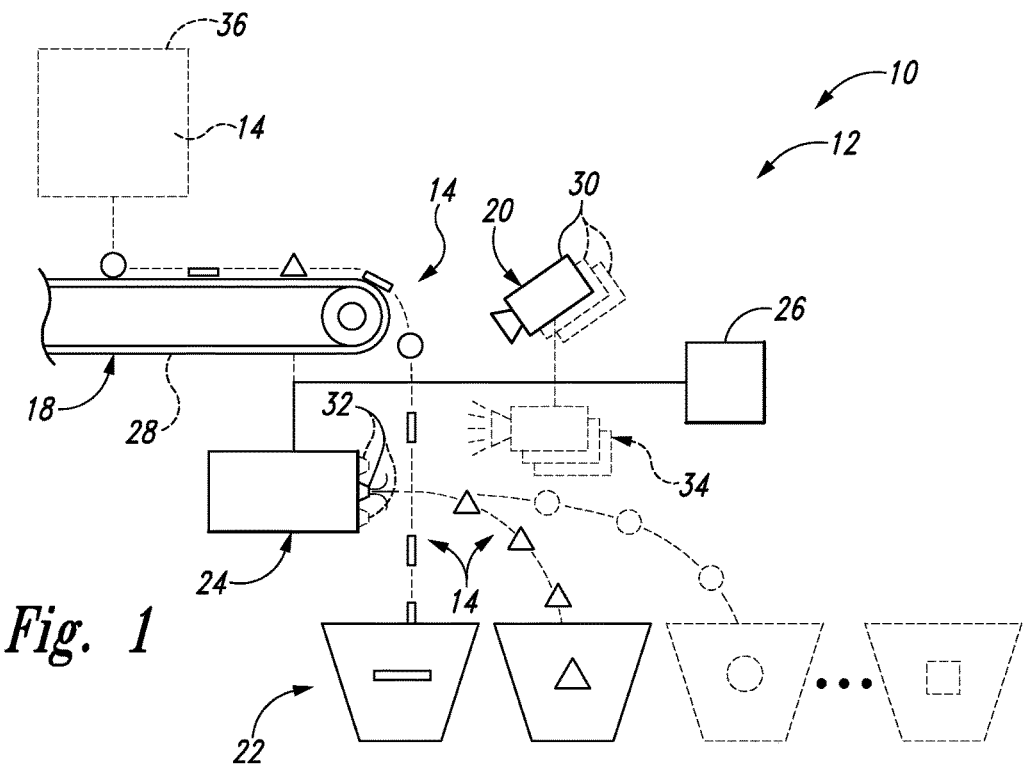
FIG. 1 is a schematic representation of systems for sorting chopped fiber composite pieces.
Figure 2:
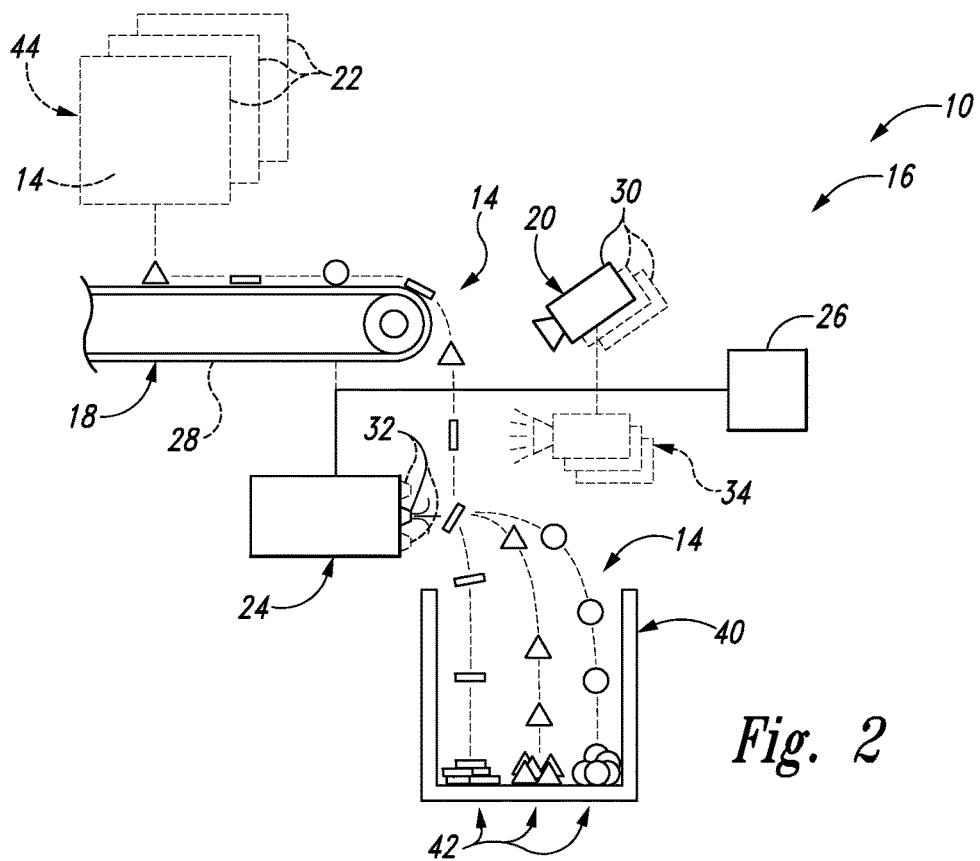
FIG. 2 is a schematic representation of systems for molding structures from chopped fiber composite pieces.

FIGS. 1 and 2 provide schematic representations of illustrative, non-exclusive examples of chopped fiber composite systems 10 according to the present disclosure. FIG. 1 illustrates a system 10 in the form of a system 12 for sorting chopped fiber composite pieces 14, such as to subsequently be used during a compression molding process, and FIG. 2 illustrates a system 16 for molding a fiber-reinforced composite structure from chopped fiber composite pieces 14. It is within the scope of the present disclosure that a system 12 and a system 16 may be distinct from each other, that a system 12 and a system 16 may be combined into a single system 10, and/or that a system 12 shares component parts with a system 16.

With reference first to FIG. 1, systems 12 for sorting chopped fiber composite pieces 14 generally include a conveyor 18, an imager 20, a plurality of receptacles 22, a pneumatic device 24, and a controller 26.

Conveyor 18 is configured to drop chopped fiber composite pieces 14 so that they fall under the force of gravity toward the receptacles 22. While the conveyor 18 in FIG. 1 is schematically illustrated in the form of an optional conveyor belt 28, conveyor 18 may be any suitable structure or mechanism that is configured to drop chopped fiber composite pieces toward the receptacles 22. Accordingly, a conveyor 18 additionally or alternatively may include and/or be a hopper or other structure that directly drops chopped fiber composite pieces, as opposed to first translating them as in the instance of a conveyor belt 28.

Additionally or alternatively, a conveyor 18 may be configured to drop chopped fiber composite pieces 14 at spaced-apart intervals in time and/or space. For example, a conveyor 18 may be configured to sequentially drop single chopped fiber composite pieces one after another. Additionally or alternatively, a conveyor 18 may be configured to drop no more than a maximum number of chopped fiber composite pieces within a certain period of time. As illustrative, non-exclusive examples, a conveyor 18 may be configured to drop no more than 100, no more than 500, no more than 1000, no more than 5000, or no more than 10000 chopped fiber composite pieces per second. Additionally or alternatively, a conveyor may be configured to drop up to or at least 100, 500, or 1000 pounds of chopped fiber composite pieces per hour.

Additionally or alternatively, a conveyor 18 may be configured to drop up to a minimum number of chopped fiber composite pieces within a certain period of time. As illustrative, non-exclusive examples, a conveyor 18 may be configured to drop up to at least 5, at least 10, at least 100, at least 500, at least 1000, at least 5000, or at least 10000 chopped fiber composite pieces per second. Moreover, a conveyor 18 may be configured to drop up to such a minimum number of chopped fiber composite pieces while having the chopped fiber composite pieces appropriately spaced apart in time and/or space for functionality of the system 10, such as based on capabilities, limitations, properties, positions, and/or characteristics of the receptacles 22 and/or the pneumatic device 24.

With continued reference to FIG. 1 and system 12, imager 20 is positioned relative to conveyor 18 and is configured to image chopped fiber composite pieces 14 as they drop from the conveyor. As schematically illustrated, an imager 20 may include one or more cameras 30 positioned to image the chopped fiber composite pieces as they drop. In some systems 12, at least two cameras or at least three cameras may be used to image chopped fiber composite pieces from different angles as they drop from the conveyor.

Any suitable imager and camera may be used and incorporated into a system 12. For example, the one or more cameras may be described as high-speed cameras and may be configured to capture images at a rate of at least 100, 500, 1000, 10000, 17000, or more images per second.

The receptacles 22 of a system 12 are positioned relative to the conveyor 18 and may take any suitable form or structure, including any suitable size and capacity, such that they are configured to receive and contain chopped fiber composite pieces 14 that drop from the conveyor 18. Moreover, any suitable number of receptacles may be provided and included as part of a system 12, such as depending on the desired sorting of chopped fiber composite pieces. Also, as discussed herein, and as schematically illustrated in FIG. 1 with the individual receptacles having schematic illustrations of distinct chopped fiber composite pieces thereon, individual receptacles may be associated with a specific characteristic of chopped fiber composite pieces, including (but not limited to) such illustrative, non-exclusive examples of characteristics as size, thickness, volume, aspect ratio of length to width, shape, color, fiber orientation, fiber number, presence of a defect, fiber pattern, orientation, reflectivity, opacity, light absorbance, geometry, and velocity.

The pneumatic device 24 of a system 12 is configured to direct pressurized streams, or bursts, of gas (e.g., air) at individual chopped fiber composite pieces 14 as they drop from the conveyor 18 so as to direct them into a specific receptacle 22, as schematically illustrated in FIG. 1. More specifically, the pneumatic device is configured to selectively direct differently configured pressurized streams, or bursts, of gas at individual chopped fiber composite pieces based on one or more characteristics of the individual chopped fiber composite pieces. This is schematically illustrated in FIG. 1 with the direction of differently shaped chopped fiber composite pieces into respective receptacles 22. The schematic shapes of the chopped fiber composite pieces used in the figures are solely for illustration purposes only and do not limit systems 10 to distinguishing between and sorting between the schematic shapes illustrated.

The differently configured pressurized streams of gas may differ based on one one or more of pressure, duration, direction, orientation, position, velocity, and temperature. For example, a higher pressure, longer duration, and/or greater velocity of a stream of gas may direct an individual chopped fiber composite piece into a receptacle that is spaced further away than a lower pressure, shorter duration, and/or lesser velocity of a stream of gas. Similarly, the direction or orientation of the stream of gas may affect to which of the receptacles 22 an individual chopped fiber composite piece is directed. Additionally or alternatively, the vertical position of the stream of gas may affect to which of the receptacles 22 an individual chopped fiber composite piece is directed, such as with a higher placed stream of gas directing a chopped fiber composite piece to a further receptacle than a lower placed stream of gas. Additionally or alternatively, the lateral position of a stream of gas may affect whether an individual chopped fiber composite piece is in a position to be directed, or redirected, by the stream of gas, such as based on the lateral position of the individual chopped fiber composite piece as it is dropped from the conveyor 18.

As schematically and optionally illustrated in FIG. 1, a pneumatic device 24 may include a plurality of spaced-apart nozzles 32. Each nozzle may be configured to direct a unique pressurized stream of gas, such as with the uniqueness based on one or more of pressure, duration, direction, orientation, position, velocity, and temperature. In some systems 12, each nozzle 32 may be configured to direct chopped fiber reinforced composite pieces into a single one of the plurality of receptacles. In some systems 12, each nozzle may be configured to direct chopped fiber reinforced composite pieces having a predetermined characteristic. Other configurations of pneumatic devices 24 and nozzles 32 also may be utilized and incorporated into a system 12.

As also schematically illustrated in FIG. 1, the controller 26 of a system 12 is in communication with the imager 20 and the pneumatic device 24. More specifically, the controller 26 is programmed to cause the pneumatic device 24 to direct a specific pressurized stream of gas at a corresponding specific chopped fiber composite piece 14 as it drops from the conveyor 18 based on image data associated with the corresponding specific chopped fiber composite piece and received from the imager 20. As a result, the specific pressurized stream of gas alters the corresponding specific chopped fiber composite piece's freefall path into a predetermined one of the plurality of receptacles based on predetermined criteria determined from the image data associated with the corresponding specific chopped fiber composite piece. In other words, as implemented by the controller 26, a system 12 is configured to detect one or more characteristics associated with an individual chopped fiber composite piece as it is dropped by the conveyor, and based on such detected characteristics, direct the individual chopped fiber composite piece into a specific one of the receptacles 22 by instructing the pneumatic device 24 to direct an appropriate pressurized stream of gas at the individual chopped fiber composite piece. Additionally, the controller may instruct the pneumatic device to not direct any stream of gas at a specific chopped fiber composite piece, such as when the specific chopped fiber composite piece is intended to drop directly into a receptacle directly beneath where the chopped fiber composite piece is dropping from the conveyor.

The predetermined criteria on which the controller bases instructions to the pneumatic device may include one or more of the illustrative, non-exclusive characteristics of chopped fiber composite pieces discussed herein.

A controller 26 may be any suitable device or devices that are configured to perform the functions of the controller discussed herein. For example, the controller may include one or more of an electronic controller, a dedicated controller, a special-purpose controller, a personal computer, a special-purpose computer, a wireless device for communication with other devices, a display device, a logic device, a memory device, and/or a memory device having computer readable media suitable for storing computer-executable instructions for implementing aspects of systems and/or methods according to the present disclosure.

As optionally and schematically illustrated in FIG. 1, some systems 12 also may include one or more light sources 34 positioned relative to the conveyor and that are configured to illuminate the chopped fiber composite pieces 14 as they drop from the conveyor and are imaged by the imager 20. For example, such illumination of the chopped fiber composite pieces may facilitate the imaging by the imager 20 and the detection of specific characteristics of the chopped composite pieces as they drop from the conveyor. As illustrative, non-exclusive examples, the light sources may be configured to emit light in one or more of, and optionally substantially only in one of, the ultraviolet, deep ultraviolet, visible, infrared, and far infrared spectrums. As used herein, the ultraviolet spectrum includes light having wavelengths generally in the range of 10-400 µm, the deep ultraviolet spectrum includes light having wavelengths generally in the range of 10-200 µm, the visible spectrum includes light having wavelengths generally in the range of 380-760 nm, the infrared spectrum includes light having wavelengths generally in the range of 750 nm-1 mm, and the far infrared spectrum includes light having wavelengths generally in the range of 10 µm-1 mm.

As also optionally and schematically illustrated in FIG. 1, a system 12 may be described as including a source 36 of the chopped fiber composite pieces 14. The source 36, when present, is positioned relative to the conveyor 18 and configured to distribute the chopped fiber composite pieces 14 on, in, and/or otherwise to the conveyor for subsequent dropping by the conveyor. The source 36 may include off-the-shelf chopped fiber composite pieces, such as provided by a supplier of such material, and with the off-the-shelf chopped fiber composite pieces optionally including desired characteristics, such as being dependent on an ultimate fiber-reinforced composite structure to be molded by a system 16. Additionally or alternatively, the source 36 may include specifically manufactured chopped fiber composite pieces, such as according to criteria specified by an operator of a system 10 and corresponding to desired characteristics of an ultimate fiber-reinforced composite structure to be molded by a system 16. Additionally or alternatively, the source 36 may include scraps of fiber-reinforced composite structures that are the result of manufacturing operations that are distinct from a system 10. For example, in the aerospace industry, many component parts of aircraft are now being constructed of fiber-reinforced composite materials, and various such component parts are constructed by various different manufacturing methods, including methods other than compression molding. In some such other manufacturing methods, fiber-reinforced composite material and parts are trimmed, resulting in what historically has been waste. Additionally, following a quality inspection of a fiber-reinforced composite part, the entire part may not be suitable for intended purpose and historically may have been scrapped as waste. Such former waste may be utilized as or turned into chopped fiber composite pieces 14 for use with systems 10 according to the present disclosure. As illustrative, non-exclusive examples, such scraps may be operated on by a grinder, a chipper, a cutter, or other suitable device to create chopped fiber composite pieces 14 for use with systems 10. Moreover, the resulting created chopped fiber composite pieces may have varying characteristics, such as corresponding to those enumerated herein, and therefore may benefit from being sorted by a system 12. Additionally, the source 36 may include a generally uniform distribution of different characteristics. Alternatively, in other systems 12, the source 36 may include a generally non-uniform distribution of different characteristics.

Turning now to FIG. 2, systems 16 for molding a fiber-reinforced composite structure from chopped composite pieces 14 generally include a conveyor 18, an imager 20, a mold 40, a pneumatic device 24, and a controller 26. Elements of systems 16 that serve a similar, or at least a substantially similar, purpose as elements of systems 12 are identified with like reference numerals and therefore may not be discussed in detail herein with reference to FIG. 2 and systems 16. As mentioned, a system 16 may be completely distinct from a system 12, may share component parts with a system 12, and/or may be combined to form a single system 10. For example, the imager of a system 16 may also be the imager of system 12, may be distinct from but the same type and/or configuration of the imager of a system 12, or may be a completely different imager than the imager of a system 12.

The mold 40 of a system 16 is positioned relative to the conveyor 18 to receive the chopped fiber composite pieces 14 as they drop from the conveyor. The mold may correspond to any desired fiber-reinforced composite structure to be formed by a compression molding process, including (but not limited to) aerospace components, land vehicle components, marine vehicle components, spacecraft components, etc. Additionally or alternatively, the fiber-reinforced composite structure may be a non-critical (or secondary) component, that is, a component whose failure is not catastrophic to the greater vehicle or other apparatus. Additionally or alternatively, the fiber-reinforced composite structure may be a critical (or primary) component.

Additionally or alternatively, the mold 40 may correspond to a fiber-reinforced composite structure that is configured to be complex, such as that includes non-uniform contours, tight corners, different thicknesses, etc., such as that may not lend itself to being manufactured via a process in which layers, or plies, of fiber-reinforced composite material are layered on a tool, mandrel, or other form. Additionally or alternatively, the mold 40 may be described as having or defining multiple regions 42 of the mold. Such regions may have different characteristics, such as corresponding to different thicknesses, different contours or radii, etc.

The pneumatic device 24 of a system 16, like the pneumatic device of a system 12, is configured to direct pressurized streams, or bursts, of gas at individual chopped fiber composite pieces 14 as they drop from the conveyor 18. However, rather than directing an individual chopped fiber reinforced composite piece into a specific receptacle, instead, the pneumatic device of a system 16 alters the freefall paths of individual chopped fiber composite pieces, such as to direct them into predetermined regions of the mold 40 and/or to alter their orientation into a desired orientation as they fall into a predetermined region of the mold. More specifically, the pneumatic device is configured to selectively direct differently configured pressurized streams, or bursts, of gas at individual chopped fiber composite pieces based on one or more characteristics of the individual chopped fiber composite pieces, such as, and including, the characteristics of chopped fiber composite pieces discussed herein in connection with systems 12. This is schematically illustrated in FIG. 2 with differently shaped chopped fiber composite pieces 14 being directed into three different regions 42 of the mold, and also with the rectangular shaped chopped fiber composite pieces being rotated from a vertical orientation to a horizontal orientation. These examples are provided solely as examples and in a very schematic manner without limiting the present disclosure to specific shapes of chopped fiber composite pieces, number of regions of a mold, etc.

The differently configured pressurized streams of gas may differ based on one or more of pressure, duration, direction, orientation, position, velocity, and temperature. For example, a higher pressure, longer duration, and/or greater velocity of a stream of gas may direct an individual chopped fiber composite piece into a region 42 of the mold 40 that is spaced further away than a lower pressure, shorter duration, and/or lesser velocity of a stream of gas. Additionally or alternatively, the direction or orientation of the stream of gas may affect a change in orientation of a chopped fiber composite piece as it drops from the conveyor and into the mold. Additionally or alternatively, the lateral position of a stream of gas may affect whether an individual chopped fiber composite piece is in a position to be directed, or redirected, by the stream of gas, such as based on the lateral position of the individual chopped fiber composite piece as it is dropped from the conveyor 18 and into the mold 40.

As schematically and optionally illustrated in FIG. 2, a pneumatic device 24 may include a plurality of spaced-apart nozzles 32. Each nozzle may be configured to direct a unique pressurized stream of gas, such as with the uniqueness based on one or more of pressure, duration, direction, orientation, position, velocity, and temperature. In some systems 16, each nozzle 32 may be configured to direct chopped fiber reinforced composite pieces into a single region of a mold. In some systems 16, each nozzle may be configured to direct chopped fiber reinforced composite pieces having a predetermined characteristic. Other configurations of pneumatic devices 24 and nozzles 32 also may be utilized and incorporated into a system 16.

In some systems 16, the pneumatic device 24 additionally or alternatively may be configured to direct heated streams of gas, and in some systems, streams of gas at a temperature that alters a physical characteristic of a chopped fiber composite piece that is impacted by the stream of gas. For example, a temperature of a stream of gas may be selected to partially cure, melt, or make tacky a chopped fiber composite piece as it is dropped into the mold. As an illustrative, non-exclusive example, heating a chopped fiber composite piece as it drops may ensure that it sticks to previously dropped chopped fiber composite pieces and/or to the mold in an intended location within the mold. Alternatively, in some systems 16, the pneumatic device may direct heated streams of gas at all chopped fiber composite pieces being dropped from the conveyor, such as to ensure a desired state of tackiness or stickiness as they drop into the mold.

The controller 26 of a system 16 is in communication with the imager 20 and the pneumatic device 24. More specifically, the controller 26 is programmed to cause the pneumatic device to direct a specific pressurized stream of gas at a corresponding specific chopped fiber composite piece 14 as it drops from the conveyor 18 based on image data associated with the corresponding specific chopped fiber composite piece and received from the imager 20. As a result, the specific pressurized stream of gas is configured to alter the corresponding specific chopped fiber composite piece's freefall path into a predetermined region of the mold and/or alters the orientation of the corresponding specific chopped fiber composite piece based on predetermined criteria determined from the image data associated with the corresponding specific chopped fiber composite piece. In other words, as implemented by the controller 26, a system 16 is configured to detect one or more characteristics associated with an individual chopped fiber composite piece as it is dropped by the conveyor 18, and based on such detected characteristics, direct the individual chopped fiber composite piece into a specific region 42 of the mold 40 and/or to alter the orientation of the individual chopped fiber composite piece by instructing the pneumatic device 24 to direct an appropriate pressurized stream of gas at the individual chopped fiber composite piece. Additionally, the controller may instruct the pneumatic device to not direct any stream of gas at a specific chopped fiber composite piece, such as when the specific chopped fiber composite piece is intended to drop directly into a region of the mold directly beneath where the chopped fiber composite piece is dropping from the conveyor.

The predetermined criteria on which the controller bases instructions to the pneumatic device may include one or more of the illustrative, non-exclusive characteristics of chopped fiber composite pieces discussed herein. As in systems 12, a controller of a system 16 may be any suitable device or devices that are configured to perform the functions of the controller discussed herein.

In some systems 16, the controller 26 may be programmed to cause the pneumatic device to uniformly, randomly, and/or pseudo-randomly distribute the chopped fiber composite pieces 14 into the mold according to characteristics of the chopped fiber composite pieces determined from the image data. In other words, systems 16 may be configured to ensure a specific distribution of differently configured chopped fiber composite pieces within the mold prior to compression and curing of the fiber-reinforced composite structure being molded.

Additionally or alternatively, in some systems 16, the controller 26 may be programmed to cause the pneumatic device 24 to heat a specific pressurized stream of gas that is directed at a specific chopped fiber composite piece 14 dropping from the conveyor 18. For example, the controller may detect or otherwise determine the state or cure, tackiness, or stickiness of a chopped fiber composite piece and determine that it should be heated to ensure that it sticks to previously dropped chopped fiber composite pieces and/or to the mold in an intended location within the mold.

As with systems 12, systems 16 also may include one or more optional light sources 34 positioned relative to the conveyor 18 and that are configured to illuminate the chopped fiber composite pieces 14 as they drop from the conveyor and are imaged by the imager 20, as schematically and optionally illustrated in FIG. 2.

As also optionally and schematically illustrated in FIG. 2, a system 16 may include a source 44 of chopped fiber composite pieces 14. The source 44, when present, is positioned relative to the conveyor and configured to distribute the chopped fiber composite pieces on and/or in the conveyor for subsequent dropping from the conveyor. As schematically indicated, the source 44 may include one or more of the receptacles 22 of a system 12.

Figure 3:
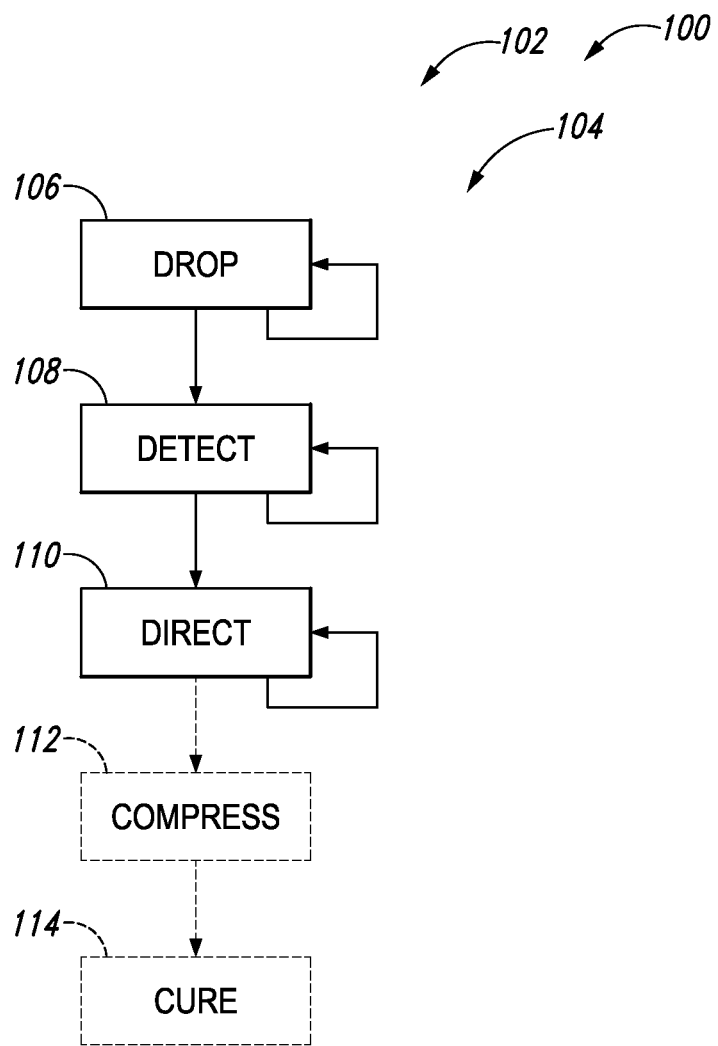
FIG. 3 is a flowchart schematically representing methods for sorting chopped fiber composite pieces and methods for molding structures from chopped fiber composite pieces.

FIG. 3 schematically provides a flowchart that represents illustrative, non-exclusive examples of methods 100 according to the present disclosure, including methods 102 for sorting chopped fiber composite pieces and methods 104 for molding a fiber-reinforced composite structure. In FIG. 3, steps shared by methods 102 and 104 and/or steps that are similar between methods 102 and methods 104 are illustrated in solid boxes. Steps that are exclusive to methods 104 are illustrated in dashed boxes. The methods and steps illustrated in FIG. 3 are not limiting and other methods and steps are within the scope of the present disclosure, including methods having greater than or fewer than the number of steps illustrated, as understood from the discussions herein.

Beginning first with methods 102, a method 102 for sorting chopped fiber composite pieces includes dropping 106 chopped fiber composite pieces, detecting 108 characteristics of individual chopped fiber composite pieces as they drop, and directing 110 individual ones of the chopped fiber composite pieces into a predetermined receptacle based on one or more detected characteristics of respective individual ones of the chopped fiber composite pieces as they drop. Steps 106, 108, and 110 are schematically illustrated in individual loops, schematically representing that the steps may be continuous and ongoing during a method 102 and not necessarily sequential in order.

The characteristics on which the directing 110 is based may include one or more of size, thickness, volume, aspect ratio of length to width, shape, color, fiber orientation, fiber number, presence of a defect, fiber pattern, orientation, reflectivity, opacity, light absorbance, geometry, and velocity.

In some methods 102, the detecting 108 may include imaging individual chopped fiber composite pieces as they drop. In some such methods, the imaging may include imaging with one or more cameras, optionally with at least two cameras positioned to image chopped fiber composite pieces from different angles as they drop from the conveyor, and optionally with at least three cameras positioned to image chopped fiber composite pieces from different angles as they drop from the conveyor. Additionally or alternatively, the imaging may include imaging at a high rate, optionally at a rate of at least 100, 500, 1000, 10000, 17000, or more images per second.

In some methods 102, the detecting also may include illuminating the chopped fiber composite pieces as they drop from the conveyor. For example, the illuminating may include illuminating with light in one or more of, and optionally substantially only in one of, the ultraviolet, deep ultraviolet, visible, infrared, and far infrared spectrums.

In some methods 102, the directing 110 may include directing differently configured pressurized streams of gas at corresponding individual chopped fiber composite pieces as they drop. For example, the differently configured pressurized streams of gas may correspond to the one or more detected characteristics of respective individual ones of the chopped fiber composite pieces. Additionally, the differently configured pressurized streams of gas may differ based on one or more of pressure, duration, direction, velocity, and temperature.

In some methods 102, the chopped fiber composite pieces may include off-the-shelf and/or specifically manufactured chopped fiber composite pieces. Additionally or alternatively, the chopped fiber composite pieces may include scraps of fiber-reinforced composite structures resultant from manufacturing operations that are distinct from sorting methods 102 and/or molding methods 104. In some methods 102, the chopped fiber composite pieces may include a generally uniform distribution of different characteristics. In other methods 102, the chopped fiber composite pieces may include a generally non-uniform distribution of different characteristics.

Next, a method 104 for molding a fiber-reinforced composite structure includes dropping 106 chopped fiber composite pieces, detecting 108 characteristics of individual chopped fiber composite pieces as they drop, directing 110 individual ones of the chopped fiber composite pieces into a predetermined region of a mold and/or altering orientations of individual ones of the chopped fiber composite pieces based on one or more detected characteristics of respective individual ones of the chopped fiber composite pieces as they drop, compressing 112 the chopped fiber composite pieces within the mold, and curing 114 the compressed chopped fiber composite pieces to define the fiber-reinforced composite structure.

In some methods 104, the directing 110 may include uniformly, randomly, and/or pseudo-randomly distributing the chopped fiber composite pieces into the mold according to characteristics of the chopped fiber composite pieces. In other words, a method 104 may ensure a specific distribution of differently configured chopped fiber composite pieces within the mold prior to compression and curing of the fiber-reinforced composite structure being molded.

In some methods 104, the method may further include and/or directing 110 may include heating individual ones or all of the chopped fiber composite pieces as they drop and are directed into the mold. For example, an individual chopped fiber composite piece may be heated based on one or more detected characteristics of the individual chopped fiber composite piece, such as whether a state or cure, tackiness, or stickiness of the individual chopped fiber composite piece. In some methods 104, the heating may be from a pressurized stream of gas.

As in methods 102, in some methods 104, the chopped fiber composite pieces may include off-the-shelf and/or specifically manufactured chopped fiber composite pieces. Additionally or alternatively, the chopped fiber composite pieces may include scraps of fiber-reinforced composite structures resultant from manufacturing operations distinct from the method. In some methods 104, the chopped fiber composite pieces may include a generally uniform distribution of different characteristics. In other methods 104, the chopped fiber composite pieces include a generally non-uniform distribution of different characteristics. Additionally or alternatively, the source of chopped fiber composite pieces used in a method 104 may come from or be the result of a sorting method 102.

Illustrative, non-exclusive examples of inventive subject matter according to the present disclosure are described in the following enumerated paragraphs:

A. A chopped fiber composite system, comprising:

a conveyor configured to drop chopped fiber composite pieces;

an imager positioned relative to the conveyor and configured to image chopped fiber composite pieces as they drop from the conveyor;

a plurality of receptacles positioned relative to the conveyor;

a pneumatic device positioned relative to the conveyor and configured to direct pressurized streams of gas at individual chopped fiber composite pieces as they drop from the conveyor; and a controller in communication with the imager and the pneumatic device, wherein the controller is programmed to cause the pneumatic device to direct a specific pressurized stream of gas at a corresponding specific chopped fiber composite piece as it drops from the conveyor based on image data associated with the corresponding specific chopped fiber composite piece and received from the imager, and wherein the specific pressurized stream of gas is configured to alter the corresponding specific chopped fiber composite piece's freefall path into a predetermined one of the plurality of receptacles based on predetermined criteria determined from the image data associated with the corresponding specific chopped fiber composite piece.

A1. The system of paragraph A, wherein the predetermined criteria includes one or more of a size of the individual chopped fiber composite piece, a thickness of the individual chopped fiber composite piece, a volume of the individual chopped fiber composite piece, a shape of the individual chopped fiber composite piece, an aspect ratio of length to width of the individual chopped fiber composite piece, color of the individual chopped fiber composite piece, fiber orientation within the individual chopped fiber composite piece, presence of a defect in the individual chopped fiber composite piece, a fiber pattern within the individual chopped fiber composite piece, number of fibers within the chopped fiber composite piece, an orientation of the individual chopped fiber composite piece, a reflectivity of the individual chopped fiber composite piece, an opacity of the individual chopped fiber composite piece, a light absorbance of the individual chopped fiber composite piece, a geometry of the individual chopped fiber composite piece, and a velocity of the individual chopped fiber composite piece.

A2. The system of any of paragraphs A-A1, wherein the imager includes one or more cameras, optionally at least two cameras positioned to image chopped fiber composite pieces from different angles as they drop from the conveyor, and optionally at least three cameras positioned to image chopped fiber composite pieces from different angles as they drop from the conveyor.

A2.1. The system of paragraph A2, wherein the one or more cameras are configured to capture images at a high rate, optionally at a rate of at least 100, 500, 1000, 10000, or 17000 images per second.

A3. The system of any of paragraphs A-A2.1, wherein the plurality of receptacles includes individual receptacles associated with at least one criterion of the predetermined criteria for receiving chopped fiber composite pieces with the respective at least one criterion.

A4. The system of any of paragraphs A-A3, wherein the pneumatic device is configured to selectively direct differently configured pressurized streams of gas at respective corresponding individual chopped fiber composite pieces, wherein the differently configured pressurized streams of gas differ based on one or more of pressure, duration, direction, orientation, position, and velocity.

A4.1. The system of paragraph A4, wherein the pneumatic device includes a plurality of nozzles.

A4.1.1. The system of paragraph A4.1, wherein each nozzle is configured to direct a unique pressurized stream of gas.

A4.1.2. The system of any of paragraphs A4.1-A4.1.1, wherein each nozzle is configured to direct chopped fiber reinforced composite pieces into a single one of the plurality of receptacles.

A4.1.3. The system of any of paragraphs A4.1-A4.1.2, wherein each nozzle is configured to direct chopped fiber reinforced composite pieces having a predetermined characteristic, wherein the predetermined characteristic corresponds to one or more of the predetermined criteria.

A5. The system of any of paragraphs A-A4.1.3, further comprising:

a light source positioned relative to the conveyor and configured to illuminate the chopped fiber composite pieces as they drop from the conveyor.

A5.1. The system of paragraph A5, wherein the light source is configured to emit light in one or more of, and optionally substantially only in one of, the ultraviolet, deep ultraviolet, visible, infrared, and far infrared spectrums.

A6. The system of any of paragraphs A-A5.1, wherein the controller includes one or more of an electronic controller, a dedicated controller, a special-purpose controller, a personal computer, a special-purpose computer, a wireless device for communication with other devices, a display device, a logic device, a memory device, and/or a memory device having computer readable media suitable for storing computer-executable instructions for implementing aspects of systems and/or methods according to the present disclosure.

A7. The system of any of paragraphs A-A6, further comprising:

a source of chopped fiber composite pieces positioned relative to the conveyor and configured to distribute the chopped fiber composite pieces on and/or in the conveyor for subsequent dropping by the conveyor.

A7.1. The system of paragraph A7, wherein the source of chopped fiber composite pieces includes off-the-shelf and/or specifically manufactured chopped fiber composite pieces.

A7.2. The system of any of paragraphs A7-A7.1, wherein the source of chopped fiber composite pieces includes scraps of fiber-reinforced composite structures resultant from manufacturing operations distinct from the system.

A7.3. The system of any of paragraphs A7-A7.2, wherein the source of chopped fiber composite pieces includes a generally uniform distribution of different characteristics, wherein the different characteristics correspond to one or more of the predetermined criteria.

A7.4. The system of any of paragraphs A7-A7.2, wherein the source of chopped fiber composite pieces includes a generally non-uniform distribution of different characteristics, wherein the different characteristics correspond to one or more of the predetermined criteria.

B. A chopped fiber composite system, comprising:
a conveyor configured to drop chopped fiber composite pieces;
an imager positioned relative to the conveyor and configured to image chopped fiber composite pieces as they drop from the conveyor;
a mold positioned relative to the conveyor to receive the chopped fiber composite pieces as they drop from the conveyor;
a pneumatic device positioned relative to the conveyor and configured to direct pressurized streams of gas at individual chopped fiber composite pieces as they drop from the conveyor; and
a controller in communication with the imager and the pneumatic device, wherein the controller is programmed to cause the pneumatic device to direct a specific pressurized stream of gas at a corresponding specific chopped fiber composite piece as it drops from the conveyor based on image data associated with the corresponding specific chopped fiber composite piece and received from the imager, and wherein the specific pressurized stream of gas is configured to alter the corresponding specific chopped fiber composite piece's freefall path into a predetermined region of the mold and/or alters the orientation of the corresponding specific chopped fiber composite piece based on predetermined criteria determined from the image data associated with the corresponding specific chopped fiber composite piece.

B1. The system of paragraph B, wherein the predetermined criteria includes one or more of a size of the individual chopped fiber composite piece, a thickness of the individual chopped fiber composite piece, a volume of the individual chopped fiber composite piece, a shape of the individual chopped fiber composite piece, an aspect ratio of length to width of the individual chopped fiber composite piece, color of the individual chopped fiber composite piece, fiber orientation within the individual chopped fiber composite piece, presence of a defect in the individual chopped fiber composite piece, a fiber pattern within the individual chopped fiber composite piece, number of fibers within the chopped fiber composite piece, an orientation of the individual chopped fiber composite piece, a reflectivity of the individual chopped fiber composite piece, an opacity of the individual chopped fiber composite piece, a light absorbance of the individual chopped fiber composite piece, a geometry of the individual chopped fiber composite piece, a velocity of the individual chopped fiber composite piece, and a state of cure of the individual chopped fiber composite piece.

B2. The system of any of paragraphs B-B1, wherein the imager includes one or more cameras, optionally at least two cameras positioned to image chopped fiber composite pieces from different angles as they drop from the conveyor, and optionally at least three cameras positioned to image chopped fiber composite pieces from different angles as they drop from the conveyor.

B2.1. The system of paragraph B2, wherein the one or more cameras are configured to capture images at a high rate, optionally at a rate of at least 100, 500, 1000, 10000, or 17000 images per second.

B3. The system of any of paragraphs B-B2.1, wherein the mold is configured to form an aerospace component, optionally a non-critical (or secondary) aerospace component, and optionally a critical (or primary) aerospace component.

B4. The system of any of paragraphs B-B3, wherein the pneumatic device is configured to selectively direct differently configured pressurized streams of gas at respective corresponding individual chopped fiber composite pieces, wherein the differently configured pressurized streams of gas differ based on one or more of pressure, duration, direction, orientation, position, velocity, and temperature.

B4.1. The system of paragraph B4, wherein the pneumatic device includes a plurality of nozzles.

B4.1.1. The system of paragraph B4.1, wherein each nozzle is configured to direct a unique pressurized stream of gas.

B4.1.2. The system of any of paragraphs B4.1-B4.1.1, wherein each nozzle is configured to direct chopped fiber reinforced composite pieces into a single predetermined region of the mold.

B4.1.3. The system of any of paragraphs B4.1-B4.1.2, wherein each nozzle is configured to direct chopped fiber reinforced composite pieces having a predetermined characteristic, wherein the predetermined characteristic corresponds to one or more of the predetermined criteria.

B5. The system of any of paragraphs B-B4.1.3, wherein the pneumatic device is configured to direct heated pressurized streams of gas at individual chopped fiber composite pieces as they drop from the conveyor.

B6. The system of any of paragraphs B-B5, further comprising:
a light source configured to illuminate the chopped fiber composite pieces as they drop from the conveyor.

B6.1. The system of paragraph B6, wherein the light source is configured to emit light in one or more of, and optionally substantially only in one of, the ultraviolet, deep ultraviolet, visible, infrared, and far infrared spectrums.

B7. The system of any of paragraphs B-B6.1, wherein the controller includes one or more of an electronic controller, a dedicated controller, a special-purpose controller, a personal computer, a special-purpose computer, a wireless device for communication with other devices, a display device, a logic device, a memory device, and/or a memory device having computer readable media suitable for storing computer-executable instructions for implementing aspects of systems and/or methods according to the present disclosure.

B8. The system of any of paragraphs B-B7, wherein the controller is programmed to cause the pneumatic device to uniformly, randomly, and/or pseudo-randomly distribute the chopped fiber composite pieces into the mold according to characteristics of the chopped fiber composite pieces determined from the image data, wherein the characteristics correspond to the predetermined criteria.

B9. The system of any of paragraphs B-B8, wherein the controller is programmed to cause the pneumatic device to heat the specific pressurized stream of gas based on the predetermined criteria.

B10. The system of any of paragraphs B-B9, further comprising:

a source of chopped fiber composite pieces positioned relative to the conveyor and configured to distribute the chopped fiber composite pieces on and/or in the conveyor for subsequent dropping from the conveyor.

B10.1. The system of paragraph B10, wherein the source of chopped fiber composite pieces includes one or more of the plurality of receptacles of the system of any of paragraphs A-A7.4.

B11. The system of any of paragraphs B-B10.1, wherein the system shares component parts with the system of any of paragraphs A-A7.4.

B12. The system of any of paragraphs B-B10.1, further comprising the system of any of paragraphs A-A7.4.

C. The system of any of paragraphs A-B12, wherein the system is configured to perform the method of any of paragraphs E-G.

D. The use of the system of any of paragraphs A-C, optionally to form a fiber-reinforced composite structure, optionally an aerospace structure.

E. A method for sorting chopped fiber composite pieces, the method comprising:

dropping chopped fiber composite pieces;

detecting characteristics of individual chopped fiber composite pieces as they drop; and directing individual ones of the chopped fiber composite pieces into a predetermined receptacle based on one or more detected characteristics of respective individual ones of the chopped fiber composite pieces as they drop.

E1. The method of paragraph E, wherein the characteristics include one or more of a size of the individual chopped fiber composite piece, a thickness of the individual chopped fiber composite piece, a volume of the individual chopped fiber composite piece, a shape of the individual chopped fiber composite piece, an aspect ratio of length to width of the individual chopped fiber composite piece, color of the individual chopped fiber composite piece, fiber orientation within the individual chopped fiber composite piece, presence of a defect in the individual chopped fiber composite piece, a fiber pattern within the individual chopped fiber composite piece, number of fibers within the chopped fiber composite piece, an orientation of the individual chopped fiber composite piece, a reflectivity of the individual chopped fiber composite piece, an opacity of the individual chopped fiber composite piece, a light absorbance of the individual chopped fiber composite piece, a geometry of the individual chopped fiber composite piece, and a velocity of the individual chopped fiber composite piece.

E2. The method of any of paragraphs E-E1, wherein the detecting includes imaging individual chopped fiber composite pieces as they drop.

E2.1. The method of paragraph E2, wherein the imaging includes imaging with one or more cameras, optionally at least two cameras positioned to image chopped fiber composite pieces from different angles as they drop from the conveyor, and optionally at least three cameras positioned to image chopped fiber composite pieces from different angles as they drop from the conveyor.

E2.2. The method of any of paragraphs E-E2.1, wherein the imaging includes imaging at a high rate, optionally at a rate of at least 100, 500, 1000, 10000, or 17000 images per second.

E3. The method of any of paragraphs E-E2.2, wherein the detecting includes illuminating the chopped fiber composite pieces as they drop from the conveyor.

E3.1. The method of paragraph E3, wherein the illuminating includes illuminating with light in one or more of, and optionally substantially only in one of, the ultraviolet, deep ultraviolet, visible, infrared, and far infrared spectrums.

E4. The method of any of paragraphs E-E3.1, wherein the directing includes directing differently configured pressurized streams of gas at corresponding individual chopped fiber composite pieces as they drop.

E4.1. The method of paragraph E4, wherein the differently configured pressurized streams of gas correspond to the one or more detected characteristics of respective individual ones of the chopped fiber composite pieces.

E4.2. The method of any of paragraphs E4-E4.1, wherein the differently configured pressurized streams of gas differ based on one or more of pressure, duration, direction, and velocity.

E5. The method of any of paragraphs E-E4.2, wherein the chopped fiber composite pieces include off-the-shelf and/or specifically manufactured chopped fiber composite pieces.

E6. The method of any of paragraphs E-E5, wherein the chopped fiber composite pieces include scraps of fiber-reinforced composite structures resultant from manufacturing operations distinct from the method.

E7. The method of any of paragraphs E-E6, wherein the chopped fiber composite pieces include a generally uniform distribution of different characteristics.

E8. The method of any of paragraphs E-E6, wherein the chopped fiber composite pieces include a generally non-uniform distribution of different characteristics.

F. A method for molding a fiber-reinforced composite structure, the method comprising:

dropping chopped fiber composite pieces;

detecting characteristics of individual chopped fiber composite pieces as they drop;

directing individual ones of the chopped fiber composite pieces into a predetermined region of a mold and/or altering orientations of individual ones of the chopped fiber composite pieces based on one or more detected characteristics of respective individual ones of the chopped fiber composite pieces as they drop;

compressing the chopped fiber composite pieces within the mold; and curing the compressed chopped fiber composite pieces to define the fiber-reinforced composite structure.

F1. The method of paragraph F, wherein the characteristics include one or more of a size of the individual chopped fiber composite piece, a thickness of the individual chopped fiber composite piece, a volume of the individual chopped fiber composite piece, a shape of the individual chopped fiber composite piece, an aspect ratio of length to width of the individual chopped fiber composite piece, color of the individual chopped fiber composite piece, fiber orientation within the individual chopped fiber composite piece, presence of a defect in the individual chopped fiber composite piece, a fiber pattern within the individual chopped fiber composite piece, number of fibers within the chopped fiber composite piece, an orientation of the individual chopped fiber composite piece, a reflectivity of the individual chopped fiber composite piece, an opacity of the individual chopped fiber composite piece, a light absorbance of the individual chopped fiber composite piece, a geometry of the individual chopped fiber composite piece, and a velocity of the individual chopped fiber composite piece.

F2. The method of any of paragraphs F-F1, wherein the detecting includes imaging individual chopped fiber composite pieces as they drop.

F2.1. The method of paragraph F2, wherein the imaging includes imaging with one or more cameras, optionally at least two cameras positioned to image chopped fiber composite pieces from different angles as they drop from the conveyor, and optionally at least three cameras positioned to image chopped fiber composite pieces from different angles as they drop from the conveyor.

F2.2. The method of any of paragraphs F-F2.1, wherein the imaging includes imaging at a high rate, optionally at a rate of at least 100, 500, 1000, 10000, or 17000 images per second.

F3. The method of any of paragraphs F-F2.2, wherein the detecting includes illuminating the chopped fiber composite pieces as they drop from the conveyor.

F3.1. The method of paragraph F3, wherein the illuminating includes illuminating with light in one or more of, and optionally substantially only in one of, the ultraviolet, deep ultraviolet, visible, infrared, and far infrared spectrums.

F4. The method of any of paragraphs F-F3.1, wherein the directing includes directing differently configured pressurized streams of gas at corresponding individual chopped fiber composite pieces as they drop.

F4.1. The method of paragraph F4, wherein the differently configured pressurized streams of gas correspond to the one or more detected characteristics of respective individual ones of the chopped fiber composite pieces.

F4.2. The method of any of paragraphs F-F4.1, wherein the differently configured pressurized streams of gas differ based on one or more of pressure, duration, direction, and velocity.

F5. The method of any of paragraphs F-F4.2, wherein the directing includes uniformly, randomly, and/or pseudo-randomly distributing the chopped fiber composite pieces into the mold according to characteristics of the chopped fiber composite pieces.

F6. The method of any of paragraphs F-F5, further comprising:
heating individual ones of the chopped fiber composite pieces concurrently with the directing.

F7. The method of any of paragraphs F-F6, wherein the chopped fiber composite pieces include off-the-shelf and/or specifically manufactured chopped fiber composite pieces.

F8. The method of any of paragraphs F-F7, wherein the chopped fiber composite pieces include scraps of fiber-reinforced composite structures resultant from manufacturing operations distinct from the method.

F9. The method of any of paragraphs F-F8, wherein the chopped fiber composite pieces include a generally uniform distribution of different characteristics.

F10. The method of any of paragraphs F-F8, wherein the chopped fiber composite pieces include a generally non-uniform distribution of different characteristics.

F11. The method of any of paragraphs F-F10, wherein the fiber-reinforced composite structure is an aerospace component, optionally a non-critical (or secondary) aerospace component, and optionally a critical (or primary) aerospace component.

F12. The method of any of paragraphs F-F11, further comprising the method of any of paragraphs E-E8.

G. The method of any of paragraphs E-F12, performed by the system of any of paragraphs A-B12.

As used herein, the terms "selective" and "selectively," when modifying an action, movement, configuration, or other activity of one or more components or characteristics of an apparatus, mean that the specific action, movement, configuration, or other activity is a direct or indirect result of user manipulation of an aspect of, or one or more components of, the apparatus.

As used herein, the terms "adapted" and "configured" mean that the element, component, or other subject matter is designed and/or intended to perform a given function. Thus, the use of the terms "adapted" and "configured" should not be construed to mean that a given element, component, or other subject matter is simply "capable of" performing a given function but that the element, component, and/or other subject matter is specifically selected, created, implemented, utilized, programmed, and/or designed for the purpose of performing the function. It is also within the scope of the present disclosure that elements, components, and/or other recited subject matter that is recited as being adapted to perform a particular function may additionally or alternatively be described as being configured to perform that function, and vice versa. Similarly, subject matter that is recited as being configured to perform a particular function may additionally or alternatively be described as being operative to perform that function.

The various disclosed elements of apparatuses and steps of methods disclosed herein are not required to all apparatuses and methods according to the present disclosure, and the present disclosure includes all novel and non-obvious combinations and subcombinations of the various elements and steps disclosed herein. Moreover, one or more of the various elements and steps disclosed herein may define independent inventive subject matter that is separate and apart from the whole of a disclosed apparatus or method. Accordingly, such inventive subject matter is not required to be associated with the specific apparatuses and methods that are expressly disclosed herein, and such inventive subject matter may find utility in apparatuses and/or methods that are not expressly disclosed herein.

The invention claimed is:

1. A method for molding a fiber-reinforced composite structure, the method comprising:
sorting chopped fiber composite pieces, wherein the sorting results in a source of chopped fiber composite pieces and comprises:
dropping chopped fiber composite pieces;
detecting characteristics of individual chopped fiber composite pieces as they drop; and
directing individual ones of the chopped fiber composite pieces into a predetermined receptacle based on one or more detected characteristics of respective individual ones of the chopped fiber composite pieces as they drop; and
following the sorting:
dropping chopped fiber composite pieces from the source;
detecting characteristics of individual chopped fiber composite pieces as they drop from the source;
directing individual ones of the chopped fiber composite pieces into a predetermined region of a mold and/or altering orientations of individual ones of the chopped fiber composite pieces based on one or more detected characteristics of respective individual ones of the chopped fiber composite pieces as they drop from the source;
compressing the chopped fiber composite pieces within the mold; and
curing the compressed chopped fiber composite pieces to define the fiber-reinforced composite structure.

2. The method of claim 1, wherein the directing includes directing differently configured pressurized streams of gas at corresponding individual chopped fiber composite pieces as they drop.

3. The method of claim 2, wherein the differently configured pressurized streams of gas correspond to the one or more detected characteristics of respective individual ones of the chopped fiber composite pieces.

4. A method for molding a fiber-reinforced composite structure, the method comprising:
dropping chopped fiber composite pieces;
detecting characteristics of individual chopped fiber composite pieces as they drop;
directing individual ones of the chopped fiber composite pieces into a predetermined region of a mold and/or altering orientations of individual ones of the chopped fiber composite pieces based on one or more detected characteristics of respective individual ones of the chopped fiber composite pieces as they drop;
compressing the chopped fiber composite pieces within the mold; and
curing the compressed chopped fiber composite pieces to define the fiber-reinforced composite structure.

5. The method of claim 4, wherein the characteristics include one or more of a size of the individual chopped fiber composite piece, a thickness of the individual chopped fiber composite piece, a volume of the individual chopped fiber composite piece, a shape of the individual chopped fiber composite piece, an aspect ratio of length to width of the individual chopped fiber composite piece, color of the individual chopped fiber composite piece, fiber orientation within the individual chopped fiber composite piece, presence of a defect in the individual chopped fiber composite piece, a fiber pattern within the individual chopped fiber composite piece, number of fibers within the chopped fiber composite piece, an orientation of the individual chopped fiber composite piece, a reflectivity of the individual chopped fiber composite piece, an opacity of the individual chopped fiber composite piece, a light absorbance of the individual chopped fiber composite piece, a geometry of the individual chopped fiber composite piece, and a velocity of the individual chopped fiber composite piece.

6. The method of claim 4, wherein the detecting includes imaging individual chopped fiber composite pieces as they drop, wherein the imaging includes imaging with at least two cameras positioned to image chopped fiber composite pieces from different angles as they drop, and wherein the imaging includes imaging at a rate of at least 100 images per second.

7. The method of claim 4, wherein the directing includes directing differently configured pressurized streams of gas at corresponding individual chopped fiber composite pieces as they drop.

8. The method of claim 7, wherein the differently configured pressurized streams of gas correspond to the one or more detected characteristics of respective individual ones of the chopped fiber composite pieces.

9. The method of claim 7, wherein the differently configured pressurized streams of gas differ based on one or more of pressure, duration, direction, and velocity.

10. The method of claim 4, wherein the chopped fiber composite pieces include off-the-shelf chopped fiber composite pieces.

11. The method of claim 4, wherein the chopped fiber composite pieces include scraps of fiber-reinforced composite structures resultant from manufacturing operations distinct from the method.

12. The method of claim 4, wherein the fiber-reinforced composite structure is an aerospace component.

13. The method of claim 4, wherein the detecting includes illuminating the chopped fiber composite pieces as they drop.

14. The method of claim 13, wherein the illuminating includes illuminating with light in one or more of the ultraviolet, deep ultraviolet, visible, infrared, and far infrared spectrums.

15. The method of claim 4, wherein the chopped fiber composite pieces include a generally uniform distribution of different characteristics.

16. The method of claim 4, wherein the chopped fiber composite pieces include a generally non-uniform distribution of different characteristics.

17. The method of claim 4, wherein the directing includes uniformly distributing the chopped fiber composite pieces into the mold according to characteristics of the chopped fiber composite pieces.

18. The method of claim 4, wherein the directing includes randomly or pseudo-randomly distributing the chopped fiber composite pieces into the mold according to characteristics of the chopped fiber composite pieces.

19. The method of claim 4, further comprising:
heating individual ones of the chopped fiber composite pieces concurrently with the directing.

20. The method of claim 19, wherein the directing includes directing differently configured pressurized streams of gas at corresponding individual chopped fiber composite pieces as they drop, wherein the pressurized streams of gas comprise heated streams of gas, and wherein the directing results in the heating.

* * * * *